United States Patent [19]

Oechslein et al.

[11] Patent Number: 5,177,110

[45] Date of Patent: Jan. 5, 1993

[54] INJECTABLE PARASITICIDAL COMPOSITION

[75] Inventors: Walter Oechslein, St. Clair, Australia; Jean-Claude Gehret, Aesch, Switzerland; Ernst Hess, Baulkham Hills, Australia; Sabine Rossow, Basel, Switzerland

[73] Assignee: Ciba-Geigy Corporation, Ardsley, N.Y.

[21] Appl. No.: 689,399

[22] Filed: Apr. 22, 1991

[30] Foreign Application Priority Data

Oct. 27, 1989 [CH] Switzerland ............... 3898-/89-4
May 15, 1991 [CH] Switzerland ............... 1109/91-8

Related U.S. Application Data

[63] Continuation-in-part of Ser. No. 602,826, Oct. 24, 1990, abandoned.

[51] Int. Cl.⁵ .............................................. A61K 31/17
[52] U.S. Cl. .................................................... 514/594
[58] Field of Search ...................................... 514/594

[56] References Cited

U.S. PATENT DOCUMENTS

| | | | |
|---|---|---|---|
| 4,557,934 | 12/1985 | Cooper | 424/128 |
| 4,677,127 | 6/1987 | Böger | 514/346 |
| 4,798,837 | 1/1989 | Drabek et al. | 514/594 |
| 4,980,506 | 12/1990 | Drabek et al. | 564/442 |

FOREIGN PATENT DOCUMENTS

| | | |
|---|---|---|
| 0255803 | 2/1988 | European Pat. Off. |
| WO86/03941 | 7/1986 | PCT Int'l Appl. |
| 2110627 | 6/1983 | United Kingdom |
| 2165846 | 4/1986 | United Kingdom |

OTHER PUBLICATIONS

Derwent Abstract, 87-189759.
Derwent Abstract, 89-043666.
Derwent & C.A. Abstracts for JP 61-263914 (Derwent 87-003713/01 & Chem. Abst. 106:162579).
Derwent & C.A. Abstracts for JP 63-002923 (Derwent 88-045802/07 & Chem. Abst. 109:176350).

*Primary Examiner*—S. J. Friedman
*Attorney, Agent, or Firm*—Edward McC. Roberts

[57] ABSTRACT

Parenterally injectable compositions for controlling parasites, which compositions contain from 0.1 to 10% of a benzoylurea as active ingredient, from 0.1 to 60% of a 1-substituted azacycloalkan-2-one, from 2 to 90% of a physiologically tolerable surfactant or mixture of surfactants and, if appropriate, as stabilizing component, from 0.05 to 15% of an acid or a buffer mixture and add 100% of a physiologically tolerable hydrophilic solvent or mixture of solvents or a mixture of physiologically tolerable hydrophilic and lipophilic solvents.

10 Claims, No Drawings

INJECTABLE PARASITICIDAL COMPOSITION

This application is a continuation-in-part of application Ser. No. 07/602,826, filed Oct. 24, 1990, now abandoned.

The present invention relates to a composition for controlling parasites harmful to animals, which composition is parenterally injectable and contains at least one sparingly soluble benzoylurea, preferably one selected from benzoylphenylureas, as active ingredient.

The term parasites does not encompass unicellular organisms.

Injectable formulations are often the most favourable form of administration because even small amounts of active ingredient can be dosed very accurately, they are easy to administer and they cause negligible distress to the animals to be treated, especially relatively large productive livestock, such as, for example, cattle, sheep, horses and donkeys. When, however, sparingly soluble substances, such as, especially, benzoylphenylureas, are used in the form of injectable formulations, problems occur in producing an effective plasma level, that is to say, and even distribution of a sufficient amount of active ingredient in the plasma, because the injected material is influenced by the tissue fluid and, for example, the physico-chemical properties of the material can thus be so changed that a considerable proportion of the injected material crystallises very rapidly and, as a result, remains at the site of injection or very close thereto. For example, benzoylphenylureas, such as N-[3-(3-chloro-5-trifluoromethylpyridyl-2-oxy)-4-chlorophenyl]-N'-[2,6-difluorobenzoyl]-urea, can be dissolved in dimethyl sulfoxide and N-methylpyrrolidone (approximately 35%; here and hereinafter, percentages are weight-per-volume percentages, i.e., 1 g ad 100 ml=1%). Although those solutions are water-miscible, they have the disadvantage that, when injected parenterally, a considerable amount of the injected material is precipitated on contact with the tissue fluid, remains at the site of injection and therefore contributes nothing to the achievement of as high a plasma level as possible. The use of such solutions is therefore uneconomical and, especially in the case of animals that are later to be slaughtered and used as food for animals or especially humans, is possible only to a limited extent owing to the local concentration of injected material. Further, in such solutions, in general benzoylphenylureas incline towards instability during storage.

Surprisingly, it has now been found that, by the addition of 1-substituted azacycloalkan-2-ones, it is possible to produce parenterally injectable formulations of sparingly soluble benzoylureas with which a very markedly increased bioavailability is achieved. As a result, the high level of activity known per se of this class of compound can be exploited even in this accurately dosable form of administration. The compositions according to the invention differ from conventional compositions in advantageous manner in that the injected material is better distributed in the plasma and therefore considerably less material has to be injected to achieve an effect of the same intensity as in the case of conventional compositions, or in that, when the same amounts of active ingredient are used, it is possible with the compositions according to the invention to maintain a high plasma level over a distinctly longer period of time than in the case of conventional compositions.

In the inventive compositions, the benzoylureas are, to a certain extent, protected against decomposition during storage.

The present invention relates to a composition for controlling parasites, which composition is parenterally injectable and contains (a) from 0.1 to 10%, preferably from 0.5 to 7% and especially for 1 to 5%, of at least one benzoylurea as active ingredient, (b) for 0.1 to 60%, preferably from 0.1 to 50%, especially from 0.5 to 10%, of a 1-substituted azacycloalkan-2-one, (c) from 2 to 90%, preferably from 40 to 85%, of a physiologically tolerable surfactant or mixture of surfactants, (d) if appropriate, as stabilising component, from 0.05 to 15%, preferably from 1.05% to 15%, especially from 2 to 7.5%, of an acid or a buffer mixture and (e) ad 100% of a physiologically tolerable hydrophilic solvent or mixture of solvents or a mixture of physiologically tolerable hydrophilic and lipophilic solvents.

The above information is to be understood as meaning that component e) is always present, that is to say, the sum of components a), b), c) and d) cannot be 100%.

Depending on the envisaged stability and in vivo tolerability of the benzoylurea formulation, also the following ranges are advantageous: a) greater than 1% but not exceeding 15%; b) 1.05% to 2.5%; c) 1.5% to 10%.

Advantageously, the type and amount of solvent is chosen first in accordance with the type and amount of active ingredient and later, if necessary, further solvent is added to the total mixture ad 100%. The solvent used to make up the amount may be that used to dissolve the active ingredient or may be a different solvent. The term "solvent" is also used here to mean "mixture of solvents".

"Parenterally injectable" is to be understood within the scope of this invention as meaning that the composition containing the dissolved active ingredient can be introduced into the body subcutaneously, intramuscularly or intravenously, for example under the skin, into the muscle tissue or into the blood vessels, by means of a cannula (injection syringe, infusion, etc.), by-passing the gastro-intestinal tract.

Intramuscular and, especially, subcutaneous administration are preferred within the scope of the present invention. According to the invention, it is possible to formulate and administer any sparingly soluble benzoylurea.

The preparation and mode of action of benzoylureas have already been described in numerous publications, for example in PCT Patent Application WO86/03941 and European Paten Applications EP-0,079,311 and EP-0,179,022.

A group of benzoylureas preferred within the scope of the present invention consists of compounds of formula I

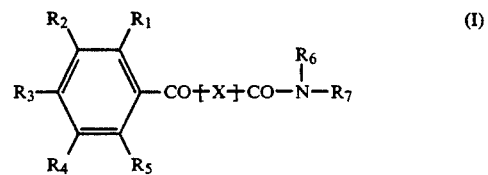

wherein
each of $R_1$, $R_2$, $R_3$ and $R_5$, independently of the others, is hydrogen, halogen, $C_1$-$C_6$alkyl, $C_1$-$C_6$haloalkyl, $C_1$-$C_6$alkoxy, $C_1$-$C_6$haloalkoxy or $C_1$-$C_6$alkylthio;

$R_4$ is hydrogen, halogen, $C_1$-$C_6$alkyl, $C_1$-$C_6$haloalkyl, $C_1$-$C_6$alkoxy, $C_1$-$C_6$haloalkoxy, $C_1C_6$alkylthio or NHR'; wherein R' is hydrogen, $R_8$CO— or $R_9$NHCO—, wherein $R_8$ is a $C_1$-$C_4$alkyl that is unsubstituted or mono- to tri-substituted by the same or different substituents from the group halogen, $C_1$-$C_4$alkoxy, $C_1$-$C_4$acyloxy and —COOG, wherein G is hydrogen, an alkali metal cation or an alkaline-earth metal cation, and $R_9$ is a $C_1$-$C_4$-alkyl or phenyl group that is unsubstituted or mono- to tri-substituted by halogen;

X is —NH— or

wherein $Y\oplus$ is an inorganic or organic cation;
$R_6$ is hydrogen or $C_1$-$C_6$alkyl; and
$R_7$ is unsubstituted or substituted phenyl, naphthyl, pyridyl, pyridazinyl, pyrimidinyl or pyrazinyl, the substituents being selected from the series halogen, especially fluorine or chlorine, alkyl, haloalkyl, alkoxy, haloalkoxy, haloalkylthio, alkenyl, haloalkenyl, alkynyl, haloalkynyl, alkylsulfinyl, alkylsulfonyl, haloalkylsulfinyl, haloalkylsulfonyl, alkylamino, dialkylamino and benzyl and also phenoxy or pyridyloxy, each of which last two substituents is substituted by substituents from the group consisting of halogen, haloalkyl, haloalkoxy and nitro, it being possible, in the case where $R_7$ is substituted phenyl, for cyano, N'-n-propyl-N'-phenylureido, an —O—$CF_2$—$CF_2$—O— bridge connecting two adjacent carbon atoms of the phenyl ring to one another, or phenoxy that is substituted by an —O—$CF_2$—$CF_2$—O— bridge connecting two adjacent carbon atoms of the phenyl ring to one another, also to be present as substituent (a phenyl ring that is substituted by an —O—$CF_2$—$CF_2$—O— bridge connecting two adjacent ring carbon atoms to one another forms a 2,2,3,4-tetrafluoro-1,4-benzodioxane radical with said bridge).

Alkyl as substituent or as part of a substituent is, insofar as the number of carbon atoms is not defined, preferably unbranched or branched $C_1$-$C_6$alkyl, especially $C_1$-$C_4$alkyl and preferably methyl.

Alkenyl and alkynyl as substituents or parts of substituents have preferably from 3 to 5 carbon atoms, the multiple bond generally being separated from the rest of the molecule by at least one carbon atom not participating in the multiple bond.

Halogen is to be understood as being fluorine, chlorine, bromine or iodine, but especially fluorine or chlorine.

In connection with $R_7$, substituents at the ring system are especially alkyl, haloalkyl, alkylthio, alkoxy and haloalkoxy groups which may be straight-chained or branched and preferably have from 1 to 4 carbon atoms. examples of such groups are, inter alia, methyl, —$CF_3$, methoxy, methylthio, —$OCF_3$, ethyl, ethoxy, n-propyl, —$CF_2$—CHF—$CF_3$, n-propoxy, —$OCF_2$—CHF—$CF_3$, isopropyl, isopropoxy, n-butyl, n-butoxy, n-pentyl, n-pentyloxy, n-hexyl and n-hexyloxy.

Prominence should be given to compounds of formula I wherein
each of $R_1$, $R_2$, $R_3$ and $R_5$, independently of the others, is hydrogen, halogen, $C_1$-$C_6$alkyl, $C_1$-$C_6$haloalkyl, $C_1$-$C_6$alkoxy, $C_1$-$C_6$haloalkoxy or $C_1$-$C_6$alkylthio;

$R_4$ is hydrogen, halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio or NHR'; wherein R' is hydrogen, $R_8$CO— or $R_9$NHCO—, wherein $R_8$ is a $C_1$-$C_4$alkyl that is unsubstituted or mono- to tri-substituted by the same or different substituents from the group halogen, $C_1$-$C_4$alkoxy, $C_1$-$C_4$acyloxy and —COOG, wherein G is hydrogen, an alkali metal cation or an alkaline-earth metal cation, and $R_9$ is a $C_1$-$C_4$-alkyl or phenyl group that is unsubstituted or mono- or tri-substituted by halogen;

X is —NH— or

wherein $Y\oplus$ is an inorganic or organic cation;
$R_6$ is hydrogen or $C_1$-$C_6$alkyl; and
$R_7$ is an unsubstituted or substituted phenyl, naphthyl, pyridyl, pyridazinyl, pyrimidinyl or pyrazinyl, the substituents being selected from the series halogen, especially fluorine or chlorine, alkyl, haloalkyl, alkoxy, haloalkoxy, alkylthio, haloalkylthio, alkenyl, haloalkenyl, alkynyl, haloalkynyl, alkylsulfinyl, alkylsulfonyl, haloalkylsulfinyl, haloalkylsulfonyl, alkylamino, dialkylamino and benzyl and also phenoxy or pyridyloxy, each of which last two substituents is substituted by halogen, haloalkyl, haloalkoxy or by nitro.

Especially preferred are representatives of formula I wherein
each of $R_1$ and $R_5$, independently of the other, is hydrogen, fluorine, chlorine, methoxy or methylthio, especially fluorine;
$R_3$ is hydrogen or fluorine and $R_4$ is hydrogen or $NH_2$,
$R_2$ is hydrogen, fluorine or chlorine, especially hydrogen;
X is —NH— or

wherein
$Y\oplus$ is $Na\oplus$, $K\oplus$ or tetraalkylammonium, such as $(n-C_4H_9)_4N\oplus$, $(CH_3)_4N\oplus$, $(C_2H_5)_4N\oplus$ or $n-C_{16}H_{33}-N\oplus(CH_3)_3$, but especially —NH—;
$R_6$ is hydrogen or $C_1$-$C_3$alkyl, preferably hydrogen, and
$R_7$ is unsubstituted or, preferably, substituted phenyl, the phenyl radical preferably being substituted by one or two halogen atoms, especially fluorine or chlorine, and, additionally, either by $C_1$-$C_6$haloalkoxy, especially $C_1$-$C_3$haloalkoxy, or by 2-pyridyloxy, the 2-pyridyloxy radical for its part being preferably substituted by $CF_3$ and halogen, especially $CF_3$ and fluorine or chlorine.

A further group of preferred benzoylureas within the scope of formula I consists of the following benzoylphenylureas of formula II

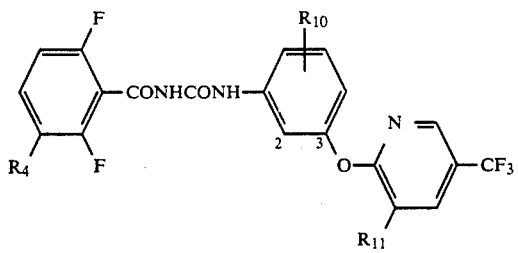

(II)

wherein
R₄ is hydrogen or NH₂;
R₁₀ is hydrogen, halogen or methyl; and
R₁₁ is hydrogen or halogen.

A preferred sub-group is formed by compounds of formula II wherein
R₄ is hydrogen or NH₂;
R₁₀ is hydrogen, fluorine, chlorine or bromine; and
R₁₁ is hydrogen, fluorine, chlorine or bromine.

Especially preferred representatives of formula II are those wherein
R₄ is hydrogen or NH₂;
R₁₀ is 4-chloro, 4-bromo or 4-methyl; and
R₁₁ is chlorine.

The compounds in the following Table are especially preferred individual representatives of compounds of formula II:

TABLE 1

Preferred benzoylphenylureas of formula II

| Compound no. | R₄ | R₁₀ | R₁₁ | m.p. [°C.] |
|---|---|---|---|---|
| 1.1 | H | 4-CH₃ | Cl | 178–179 |
| 1.2 | H | 4-Br | Cl | 198–200 |
| 1.3 | H | 4-CH₃ | H | 188–189 |
| 1.4 | H | 4-F | Cl | 174–177 |
| 1.5 | H | 4-Cl | Cl | 185–189 |
| 1.6 | H | 4-F | H | 185–188 |
| 1.7 | H | 4-Cl | H | 185–188 |
| 1.8 | H | H | Cl | 172–173 |
| 1.9 | H | H | H | 186–188 |
| 1.10 | H | 4-Br | H | |
| 1.11 | H | H | Br | |
| 1.12 | H | H | I | |
| 1.13 | H | 4-Br | Br | |
| 1.14 | H | 4-CH₃ | F | |
| 1.15 | H | 5-CH₃ | H | |
| 1.16 | H | 5-CH₃ | Cl | |
| 1.17 | H | 5-CH₃ | F | |
| 1.18 | H | 6-CH₃ | Cl | |
| 1.19 | H | 6-F | Cl | |
| 1.20 | H | 6-Cl | Cl | |
| 1.21 | H | 6-Cl | F | |
| 1.22 | H | 6-Cl | H | |
| 1.23 | H | H | F | |
| 1.24 | NH₂ | 4-Cl | Cl | 181–182 |

Preferred embodiments of the present invention contain as active ingredient one of the benzoylureas listed below, which is not, however, exhaustive.

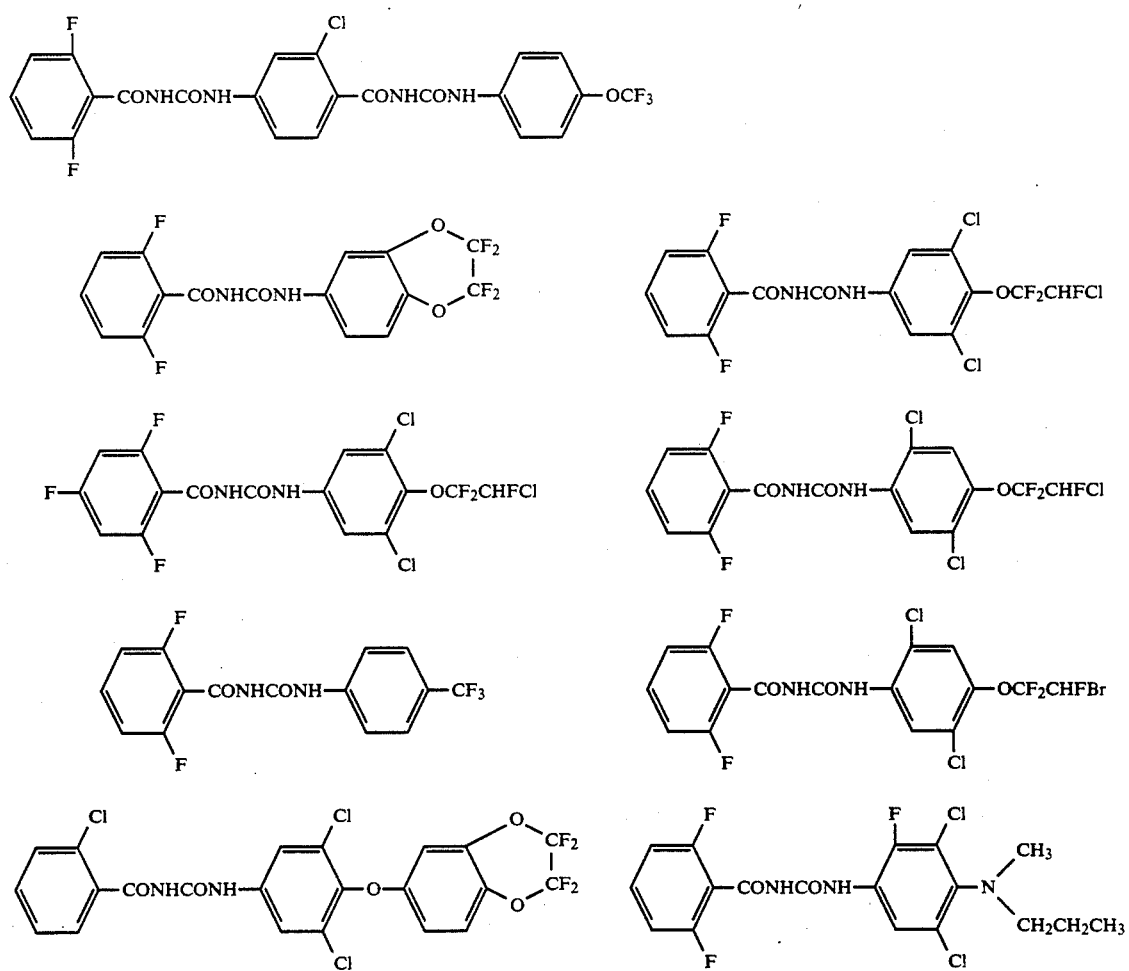

-continued
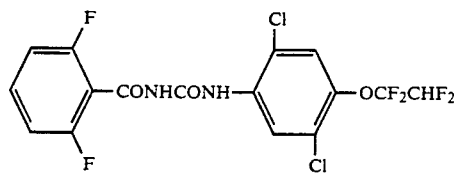
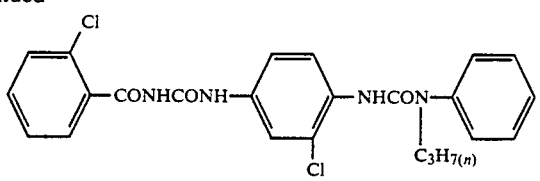
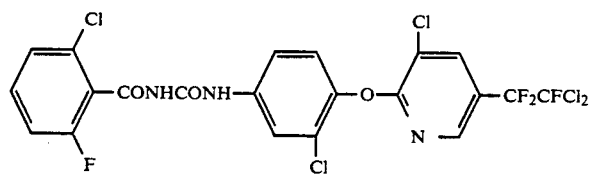
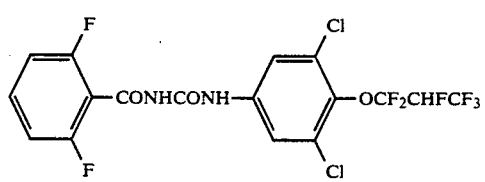
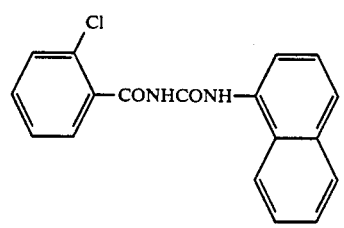
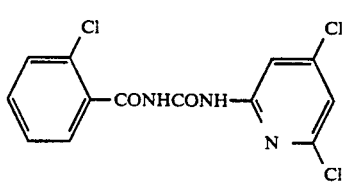
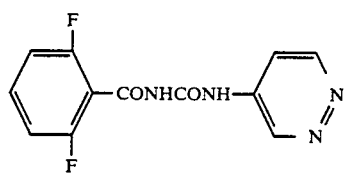
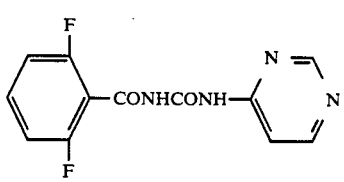
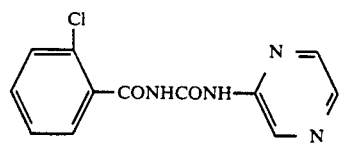
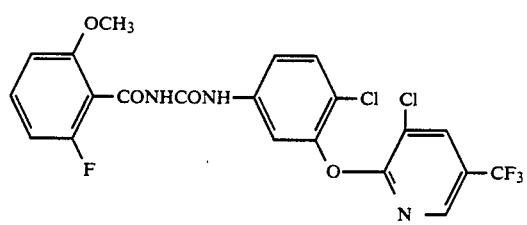
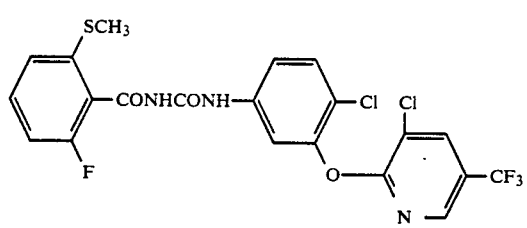
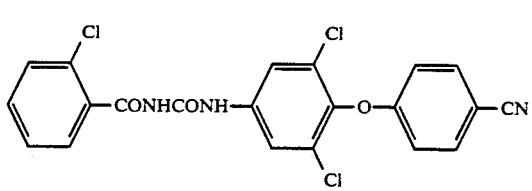
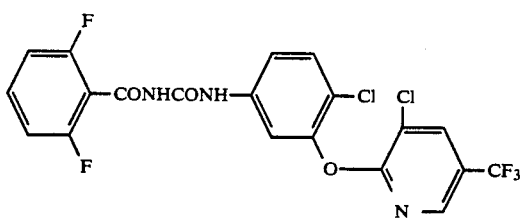
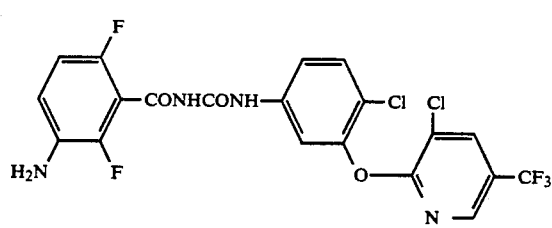
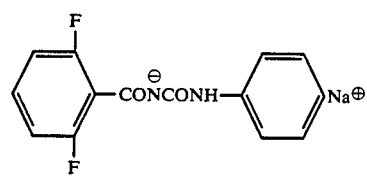
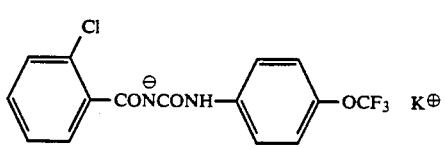

-continued
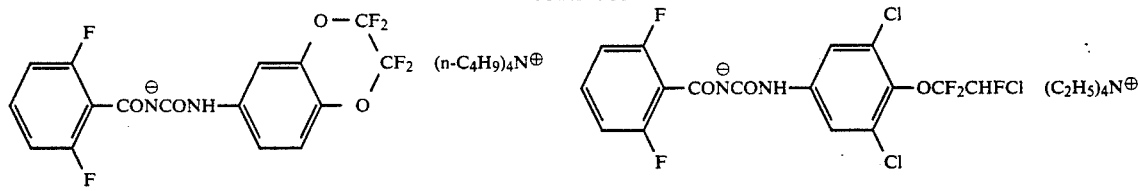
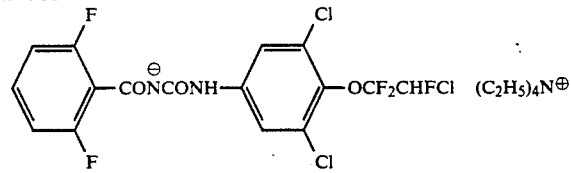
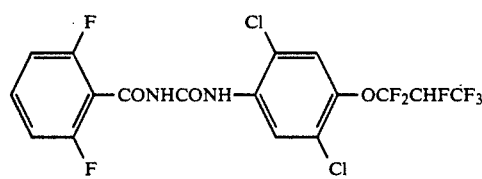
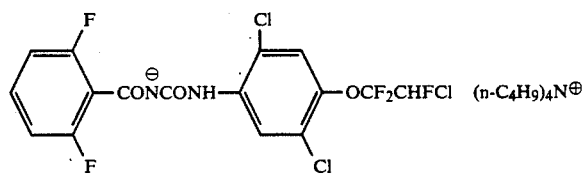
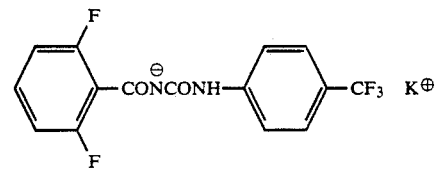
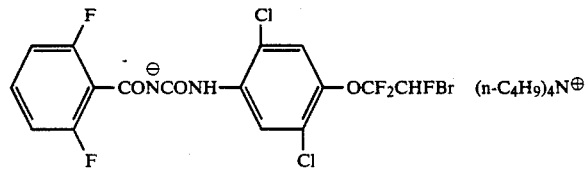
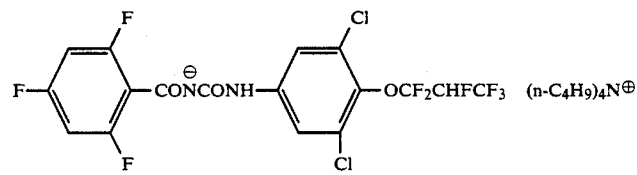
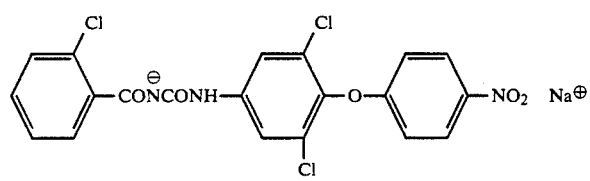
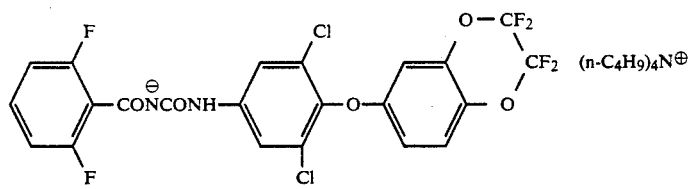
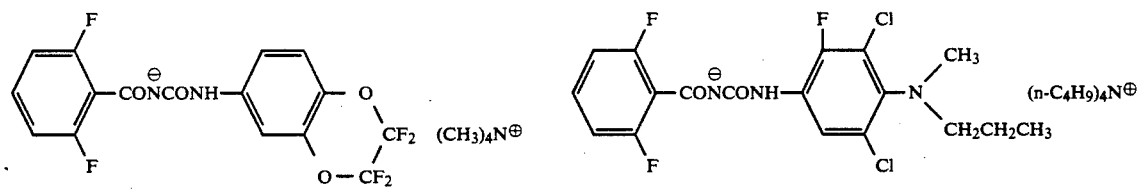
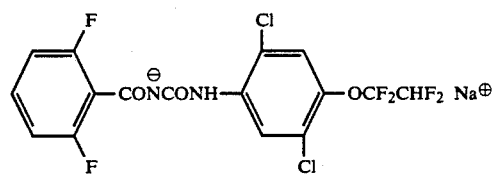
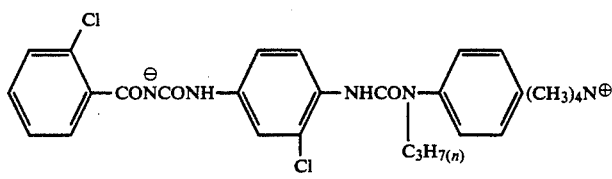
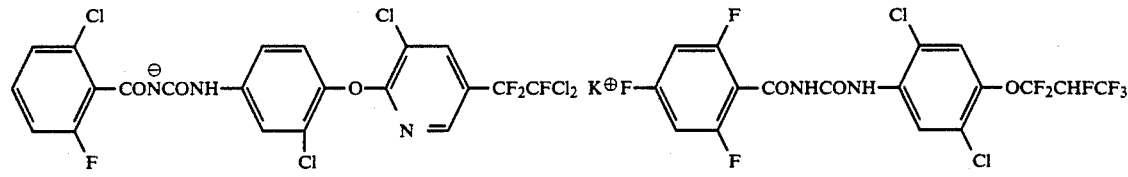
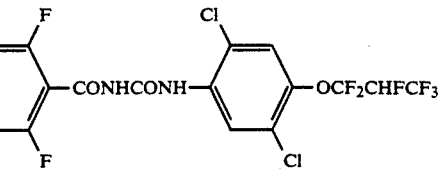

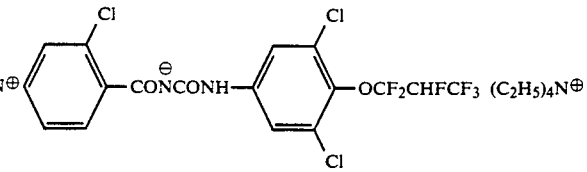

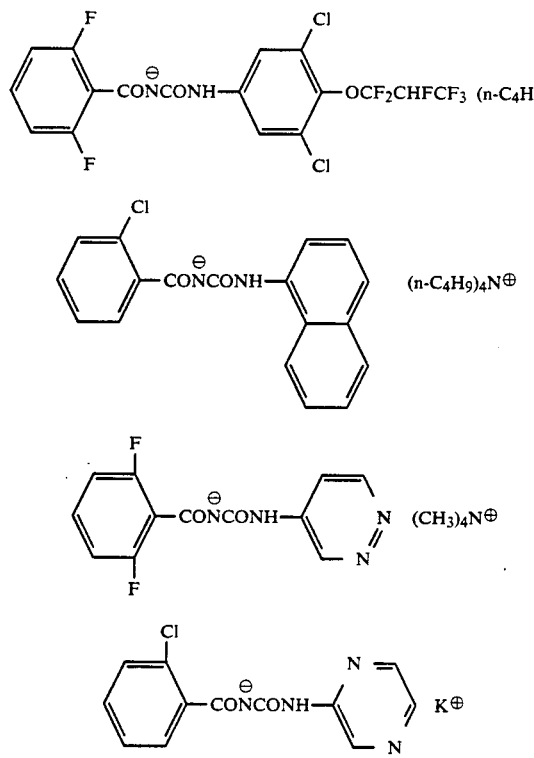

Especially preferred are formulations according to the invention that contain N-[3-(3-chloro-5-trifluoromethylpyridyl-2-oxy)-4-chlorophenyl]-N'-[2,6-difluorobenzoyl]-urea or N-[3-(3-chloro-5-trifluoromethylpyridyl-2-oxy)-4-chlorophenyl]-N'-[2,6-difluoro-3-aminobenzoyl]-urea as active ingredient.

Within the scope of the present invention, 1-substituted azacycloalkan-2-ones shall be understood as being compounds of formula III $$\underset{O}{\overset{(CH_2)_n-N-R}{\underset{\|}{C}}} \quad (III)$$

wherein n is an integer from 2 to 7 and R is a $C_6$–$C_{15}$alkyl which may be interrupted by an oxygen atom. R is preferably an unbranched $C_{10}$–$C_{14}$alkyl, especially n-dodecyl. Of the 1-substituted azacycloalkan-2-ones, 1-n-dodecylazacycloheptan-2-one (Azone ®) and 1-n-dodecylazacyclopentan-2-one are especially preferred.

The use of 1-substituted azacycloalkan-2-ones, including azone (Azone ®), as penetration enhancers in transdermal systems (penetration into and through the skin after topical administration) is known, for example, from U.S. Pat. No. 4,557,934 and the corresponding patent publication EP 0 129 284. Those references describe the carrier function of 1-substituted azacycloalkan-2-ones, which amounts to an improved penetration of the skin barrier in the case of certain active ingredients. Japanese Patent Applications JP 63-002 923 and JP 61-263914 disclose azone as a formulation auxiliary in preparations for controlling tumours.

Within the scope of the present invention, suitable physiologically tolerable surfactants are especially non-ionic surfactants.

Within the scope of the present invention, suitable physiologically tolerable surfactants are especially non-ionic surfactants having a molecular weight of less than 20,000, preferably less than 5,000, that belong to the group defined below:

(1) Polyethoxylated triglycerides, (2) polyethoxylated hydroxystearic acid esters, (3) polyethoxylated sorbitan fatty acid esters, (4) sorbitan fatty acid esters, (5) polyethoxylated methyl glucoside sesquistearates, (6) fatty acid sugar esters, (7) polyethoxylated fatty acid amines and (10) polyethoxy/polypropoxy block polymers [preferably block polymers having HLB values (HLB: hydrophilic-lipophilic balance) of 12-20].

Of the polyethoxylated triglycerides, hydroxystearic acid esters, sorbitan fatty acid esters, methyl glucoside sesquistearates, fatty alcohol ethers, fatty acid esters and fatty acid amines, mention may be made especially of those having from 2 to 100, especially from 10 to 40 and, more especially, 10, 20 or 40 ethylene oxide units.

Of the polyethoxy/polypropoxy block polymers, those having an ethylene oxide content of from 20 to 80% should be given prominence.

Especially suitable representatives of the group listed above are (EO=number of ethylene oxide units):

(1)

Polyethoxylated castor oil (EO 40), commercially available under the name CREMOPHOR ® EL (BASF AG);

Polyethoxylated, hydrogenated castor oil (EO 40, EO60), commercially available under the name CREMOPHOR ® RH 40, RH60, (BASF AG);

(2)

Polyethoxylated 12-hydroxystearic acid ester (EO 15), commercially available under the name SOLUTOL ® HS 15 (BASF);

(3)

Polyethoxylated sorbitan monolaurate (EO 20), commercially available under the name TWEEN® 20 ICI);
Polyethoxylated sorbitan monopalmitate (EO 20), commercially available under the name TWEEN® 40 (ICI);
Polyethoxylated sorbitan monostearate (EO 20), commercially available under the name TWEEN® 60 (ICI);
Polyethoxylated sorbitan monooleate (EO 20), commercially available under the name TWEEN® 80 (ICI);
Polyethoxylated sorbitan tristearate (EO 20), commercially available under the name TWEEN® 65 (ICI);
Polyethoxylated sorbitan trioleate (EO 20), commercially available under the name TWEEN® 85 (ICI);

(4)

Sorbitan monolaurate, commercially available under the name SPAN® 20 (ICI);
Sorbitan monopalmitate, commercially available under the name SPAN® 40 (ICI);
Sorbitan monostearate, commercially available under the name SPAN® 60 (ICI);
Sorbitan monooleate, commercially available under the name SPAN® 80 (ICI);
Sorbitan tristearate, commercially available under the name SPAN® 65 (ICI);
Sorbitan trioleate, commercially available under the name SPAN® 85 (ICI);

(5)

Polyethoxylated methyl glucoside sesquistearate (EO 20), commercially available under the name GLUCAMATE® SSE-20 (Amerchol Corp.);

(6)

12-hydroxystearin saccharose ester,
saccharose monolaurate,
saccharose monomyristate,
saccharose monopalmitate,
saccharose monooleate,
saccharose monostearate,
saccharose distearate
saccharose dioleate,
saccharose dipalmitate,
Saccharose mono-/di-/tri-palmitate/stearate products are commercially available, for example under the names CRODESTA® DKS F10, F20, F50, F70, F110, F140, F160 (Croda Chemicals Ltd.);
Saccharose monococoate, commercially available under the name CRODESTA® SL40 (Croda Chemicals Ltd.);

(7)

Polyethoxylated oleyl alcohol ether (EO 2), commercially available under the names AMEROXOL® OE-2 (Amerchol Europe) and Brij 92 (Atlas Chemie/ICI);
Polyethoxylated oleyl alcohol ether (EO 10), commercially available under the names AMEROXOL® OE-10 (Amerchol Europe) and Brij 96 (Atlas Chemie/ICI);
Polyethoxylated oleyl alcohol ether (EO 20), commercially available under the names AMEROXOL® OE-20 (Amerchol Europe) and Brij 98 (Atlas Chemie/ICI);

(8)

Polyethoxylated stearate (EO 8, EO20, EO30, EO40*, EO50, EO100), commercially available under the names Myrj® 45, 49, 51, (52, 52C, 52S)*, 53, 59 (ICI);
Polyethoxylated laurate (in the form of dilaurate) (EO 5, EO 10), commercially available under the name Pegosperse® 200-DL (Glyco Inc.);
Polyethoxylated cocoate (EO 7), commercially available under the name CETIOL® HE (Henkel Corp.);

(9)

Polyethoxylated tallow fatty amine (EO 10), commercially available under the name GENAMIN® T100 (Hoechst AG);

(10)

Ethylene oxide/propylene oxide block polymer having a molecular weight of approximately 16,000 and an ethylene oxide content of 80%, commercially available under the name PLURONIC® F-108 (BASF Wyandotte Corp.);
Ethylene oxide/propylene oxide block polymer having a molecular weight of approximately 4500 and an ethylene oxide content of 50%, commercially available under the name PLURONIC® P-85 (BASF Wyandotte Corp.);
Ethylene oxide/propylene oxide block polymer having a molecular weight of approximately 1450 and an ethylene oxide content of 20%, commercially available under the name PLURONIC® L-42 (BASF Wyandotte Corp.);
Ethylene oxide/propylene oxide block polymer having a molecular weight of approximately 2900 and an ethylene oxide content of 40%, commercially available under the name SYNPERONIC® PE L 64 (ICI) and Pluronic L 64 (BASF Wyandotte Corp.).

The above trade names for surfactants are to be understood as being only examples and not limitations.

Within the scope of the present invention, the following surfactants (A to F) and mixtures of surfactants (X to Z) have proved to be especially suitable:
A) Polyethoxylated castor oil (EO 40);
B) Polyethoxylated hydrogenated castor oil (EO 40);
C) Polyethoxylated 12-hydroxystearic acid ester (EO 15);
D) Polyethoxylated oleyl alcohol ether (EO 10);
E) Polyethoxylated laurate (in the form of dilaurate; molecular weight 200, 400, EO 5, EO 10);
F) Ethylene oxide/propylene oxide block polymer (molecular weight 2900, ethylene oxide content 40%);
X) Mixture of A) and B), preferably in the ratio A:B=2:1 to 1:2, especially 1:1;
Y) Mixture of C) and E), preferably in the ratio C:E=2:1 to 1:2, especially 1:1;
Z) Mixture of A) and E), preferably in the ratio A:E=3:1 to 1:2, especially 1:1 to 1.5:1.

Non-ionic surfactants, such as can be used within the scope of the present invention, are known from standard works of the relevant literature. The following may be mentioned as examples of such standard works:
Ash, M. and I., Encyclopedia of Surfactants, Chemical Publishing Co. Inc., New York, N.Y. (Vol. I, 1980; Vol. II, 1981; Vol. III, 1981; Vol. IV, 1985);

1986 International McCutcheon's Emulsifiers & Detergents, The Manufacturing Confectioner Publishing Co., Glen Rock, N.J., USA;

Stache, H., Tensid-Taschenbuch, Carl Hanser Verlag, Munich, Vienna, 1981.

Within the scope of the present invention, suitable physiologically tolerable hydrophilic solvents are those belonging to the group listed below:

a) Monohydroxyalkyl groups having from 2 to 10 carbon atoms, b) acyclic saturated polyols, c) dimethyl sulfoxide, d) glycerol formal, e) 2,2-dimethyl-4-hydroxymethyl-1,3-dioxolane (solketal), f) tetrahydrofurfuryl alcohol (polyethoxy) ether (glycofurol), g) water and h) N-methylpyrrolidone.

There may be mentioned as examples of representatives of sub-group a): ethanol, 1-propanol, 2-propanol, 2-butanol, tert.-butyl alcohol, 1-hexanol, 1-heptanol, 2-heptanol, 1-octanol, 2-octanol, 1-nonanol and 1-decanol.

Examples of representatives of sub-group b) are especially polyols having from 2 to 6, preferably 3 or 4, carbon atoms and 2 or 3 hydroxy groups, such as 1,2-propanediol, glycerol, 1,2-butanediol, 1,3-butanediol and corresponding polyols etherified by lower alkyl groups, especially methyl groups, such as, for example, 1,2-propanediol-1-methyl ether, and, in addition, polyethylene glycols having an average molar mass in the range of from 200 to 600, such as, for example, polyethylene glycol 300 (commercially available, for example, under the name PLURIOL E300, BASF).

Suitable lipophilic solvents are especially esters of carboxylic acids, for example ethyl acetate, n-propyl acetate and n-butyl acetate, and liquid waxes, such as, for example, isopropyl myristate, isopropyl palmitate, lauric acid hexyl ester and ethyl oleate.

In the case of mixtures of hydrophilic and lipophilic solvents, the proportion of lipophilic solvent is advantageously from 0.1 to 30%, based on the total amount of solvent.

Within the scope of the present invention it is possible to use any surfactant and solvent normally suitable for administration in veterinary medicine.

Acids suitable as stabilising component within the scope of this invention are especially organic acids having from 2 to 6 carbon atoms. Examples of suitable acids are citric acid, ascorbic acid, lactic acid, acetic acid, malic acid and tartaric acid.

Suitable as stabilising buffer mixtures within the scope of the instant invention are physiologically tolerable buffer mixtures customarily used in human medicine or in veterinary medicine, preferably mixtures consisting of one of the acids mentioned above and of one of its salts.

The preferred embodiments of the injectable parasiticidal compositions according to the invention include, for example, the following compositions:

(A) From 0.1 to 10% of a benzoylphenylurea, from 0.5 to 10% of a 1-substituted azacycloalkan-2-one, from 2 to 90% of a surfactant or mixture of surfactants, from 0.05 to 15% of a stabiliser and ad 100% of solvent;

(B) From 0.5 to 7% of a benzoylphenylurea, from 0.5 to 10% of a 1-substituted azacycloalkan-2-one, from 2 to 90% of a surfactant or mixture of surfactants, from 0.05 to 15% of a stabiliser and ad 100% of solvent;

(C) From 1 to 5% of a benzoylphenylurea, from 0.5 to 10% of a 1-substituted azacycloalkan-2-one, from 2 to 90% of a surfactant or mixture of surfactants, from 0.05 to 15% of a stabiliser and ad 100% of solvent;

(D) From 0.1 to 10% of a benzoylphenylurea, from 0.1 to 50% of a 1-substituted azacycloalkan-2-one, from 2 to 90% of a surfactant or mixture of surfactants, from 0.05 to 15% of a stabiliser and ad 100% of solvent;

(E) From 0.5 to 7% of a benzoylphenylurea, from 0.5 to 50% of a 1-substituted azacycloalkan-2-one, from 2 to 90% of a surfactant or mixture of surfactants, from 0.05 to 15% of a stabiliser and ad 100% of solvent;

(F) From 1 to 5% of a benzoylphenylurea, from 0.1 to 50% of a 1-substituted azacycloalkan-2-one, from 2 to 90% of a surfactant or mixture of surfactants, from 0.05 to 15% of a stabiliser and ad 100% of solvent;

(G) From 0.1 to 10% of a benzoylphenylurea, from 0.1 to 60% of a 1-substituted azacycloalkan-2-one, from 2 to 90% of a surfactant or mixture of surfactants, from 0.05 to 15% of a stabiliser and ad 100% of solvent;

(H) From 0.5 to 7% of a benzoylphenylurea, from 0.1 to 60% of a 1-substituted azacycloalkan-2-one, from 2 to 90% of a surfactant or mixture of surfactants, from 0.05 to 15% of a stabiliser and ad 100% of solvent;

(I) From 1 to 5% of a benzoylphenylurea, from 0.1 to 60% of a 1-substituted azacycloalkan-2-one, from 2 to 90% of a surfactant or mixture of surfactants, from 0.05 to 15% of a stabiliser and ad 100% of solvent.

Within the combinations (A) to (I), specific embodiments that are especially preferred are those wherein the active ingredient is N-[3-(3-chloro-5-trifluoromethylpyridyl-2-oxy)-4-chlorophenyl]-N'-[2,6-difluorobenzoyl]-urea or N-[3-(3-chloro-5-trifluoromethylpyridyl-2oxy)-4-chlorophenyl]-N'-[2,6-difluoro-3-aminobenzoyl]-urea.

Also especially preferred within the combinations (A) to (I) are those wherein the 1-substituted azacycloalkan-2-one is n-dodecylazacycloheptan-2-one or n-dodecylazacyclopentan-2-one.

The present invention relate also to a process for the preparation of an injectable composition for controlling parasites in and on productive livestock and domestic animals, which composition is parenterally injectable and contains from 0.1 to 10% of a benzoylurea as active ingredient, from 0.1 to 60% of a 1-substituted azacycloalkan-2-one, from 2 to 90% of a physiologically tolerable surfactant or mixture of surfactants and, if appropriate, as stabilising component, from 0.05 to 15% of an acid or a buffer mixture and ad 100% of a physiologically tolerable hydrophilic solvent or mixture of solvents or a mixture of physiologically tolerable hydrophilic and lipophilic solvents, which process comprises dissolving the benzoylurea in a hydrophilic solvent and mixing the solution with the surfactant and the 1-substituted azacycloalkan-2-one, and, if appropriate, with the lipophilic solvent and, if appropriate, with a stabiliser, making up the batch with a solvent and sterile-filtering the resulting final mixture through a filter and then, if desired, subjecting it to heat sterilisation.

The injectable compositions according to the invention are effective against a large number of multicellular parasites, especially against ectoparasites in and on domestic animals and productive livestock, such as insects of the orders Homoptera, Heteroptera, Diptera, Thysanoptera, Orthoptera, Anoplura, Siphonaptera, Psocoptera and Hymenoptera and also arachnida of the order Acarina, especially the sub-order Ixodida (ticks). The compositions according to the invention also exhibit a good anthelmintic action. They are suitable for controlling parasitic nematodes, for example of the orders Rhabditida, Ascaridida, Spirurida and Trichocephalida, or for controlling cestodes of the orders Cyclophyllidae and Pseudophillidae or for controlling trematodes of the order Digenea in domestic animals and productive livestock.

Domestic animals and productive livestock are to be understood as being, for example, cattle, sheep, goats, horses, pigs, cats and dogs.

The particular advantage of the compositions according to the invention resides in the fact that they can be used systemically by administering them locally and thus spreading them through the whole animal via the blood plasma and tissue fluid.

The present invention accordingly relates also to a method for the systemic control of multicellular parasites in and on productive livestock and domestic animals, which comprises the prophylactic or curative parenteral injection of the composition according to the invention into the animal.

In addition, the present invention relates to the use of 1-substituted azacycloalkan-2-ones in benzoylurea-based veterinary medicinal preparations for controlling multicellular endo- and ecto-parasites.

EXAMPLES

Formulation of Compositions According to the Invention

| Example F-1: | |
| --- | --- |
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| dimethyl sulfoxide | 20.0 g |
| lauric acid hexyl ester | 5.0 g |
| 1-n-dodecylazacycloheptan-2-one | 5.0 g |
| n-propyl acetate | ad 100 ml |
| Example F-2: | |
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| dimethyl sulfoxide | 20.0 g |
| lauric acid hexyl ester | 5.0 g |
| 1-n-dodecylazacycloheptan-2-one | 10.0 g |
| n-propyl acetate | ad 100 ml |
| Example F-3: | |
| N-[3-(3-chloro-5-trifluoromethylpyridyl-2-oxy)-4-chlorophenyl]-N'-[2,6-difluoro-3-aminobenzoyl]-urea | 2.5 g |
| polyethoxylated castor oil (EO 40) | 40.0 g |
| dimethyl sulfoxide | 20.0 g |
| lauric acid hexyl ester | 5.0 g |
| 1-n-dodecylazacycloheptan-2-one | 5.0 g |
| n-propyl acetate | ad 100 ml |
| Example F-4: | |
| N-[3-(3-chloro-5-trifluoromethylpyridyl-2-oxy)-4-chlorophenyl]-N'-[2,6-difluoro-3-aminobenzoyl]-urea | 2.5 g |
| polyethoxylated castor oil (EO 40) | 40.0 g |
| dimethyl sulfoxide | 20.0 g |
| lauric acid hexyl ester | 5.0 g |
| 1-n-dodecylazacycloheptan-2-one | 10.0 g |
| n-propyl acetate | ad 100 ml |
| Example F-5: | |
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| PEG-200 dilaurate | 42.5 g |
| citric acid | 0.25 g |
| 1-n-dodecylazacycloheptan-2-one | 5.0 g |
| N-methylpyrrolidone | ad 100 ml |
| Example F-6: | |
| N-[3-(3-chloro-5-trifluoromethylpyridyl-2-oxy)-4-chlorophenyl]-N'-[2,6-difluorobenzoyl]-urea | 2.500 g |
| polyethoxylated castor oil (EO 40) | 40.000 g |
| PEG-200 dilaurate | 32.500 g |
| 1-n-dodecylazacycloheptan-2-one | 2.500 g |
| acetic acid | 2.500 g |
| sodium acetate | 0.025 g |
| N-methylpyrrolidone | ad 100 ml |
| Example F-7: | |
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| PEG-200 dilaurate | 32.5 g |
| 1-n-dodecylazacycloheptan-2-one | 2.5 g |
| acetic acid | 7.5 g |
| N-methylpyrrolidone | ad 100 ml |
| Example F-8: | |
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 42.5 g |
| PEG-200 dilaurate | 30.0 g |
| 1-n-dodecylazacycloheptan-2-one | 5.0 g |
| lactic acid | 5.0 g |
| N-methylpyrrolidone | ad 100 ml |
| Example F-9: | |
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| PEG-200 dilaurate | 42.5 g |
| citric acid | 1.25 g |
| 1-n-dodecylazacycloheptan-2-one | 5.0 g |
| N-methylpyrrolidone | ad 100 ml |
| Example F-10: | |
| N-[3-(3-chloro-5-trifluoromethylpyridyl-2-oxy)-4-chlorophenyl]-N'-[2,6-difluoro-3-aminobenzoyl]-urea | 2.500 g |
| polyethoxylated castor oil (EO 40) | 40.000 g |
| PEG-200 dilaurate | 32.500 g |
| acetic acid | 2.500 g |
| sodium acetate | 0.025 g |
| 1-n-dodecylazacycloheptan-2-one | 2.500 g |
| N-methylpyrrolidone | ad 100 ml |
| Example F-11: | |
| N-[3-(3-chloro-5-trifluoromethylpyridyl-2-oxy)-4-chlorophenyl]-N'-[2,6-difluoro-3-aminobenzoyl]-urea | 2.5 g |
| polyethoxylated castor oil (EO 40) | 40.0 g |
| PEG-200 dilaurate | 32.5 g |
| 1-n-dodecylazacycloheptan-2-one | 2.5 g |
| acetic acid | 7.5 g |
| N-methylpyrrolidone | ad 100 ml |
| Example F-12: | |
| N-[3-(3-chloro-5-trifluoromethylpyridyl-2-oxy)-4-chlorophenyl]-N'-[2,6-difluoro-3-aminobenzoyl]-urea | 2.5 g |
| polyethoxylated castor oil (EO 40) | 42.5 g |
| PEG-200 dilaurate | 30.0 g |
| 1-n-dodecylazacycloheptan-2-one | 5.0 g |
| lactic acid | 5.0 g |
| N-methylpyrrolidone | ad 100 ml |
| Example F-13: | |
| N-[3-(3-chloro-5-trifluoromethylpyridyl-2-oxy)-4-chlorophenyl]-N'-[2,6-difluoro-3-aminobenzoyl]-urea | 2.5 g |
| polyethoxylated castor oil (EO 40) | 40.0 g |
| PEG-200 dilaurate | 32.5 g |
| 1-n-dodecylazacycloheptan-2-one | 2.5 g |
| acetic acid | 2.5 g |

-continued

| | |
|---|---|
| N-methylpyrrolidone | ad 100 ml |

Example F-14:

| | |
|---|---|
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| PEG-200 dilaurate | 32.5 g |
| 1-n-dodecylazacycloheptan-2-one | 2.5 g |
| acetic acid | 2.5 g |
| N-methylpyrrolidone | ad 100 ml |

BIOLOGICAL EXAMPLE

Bioavailability (plasma concentration)

In order to investigate bioavailability in vivo, formulations F-1 to F-12 according to the invention are each administered once subcutaneously to each of 4 cattle of from 200 to 300 kg body weight (BW) at a dose of 1 mg/kg BW. For comparison purposes, the control group, consisting of 4 cattle, receives the active ingredient in the following formulation:

| | |
|---|---|
| N-[3-(3-chloro-5-trifluoromethylpyridyl-2-oxy)-4-chlorophenyl]-N'-[2,6-difluorobenzoyl]-urea | 2.5 g |
| polyethoxylated castor oil (EO 40) | 40.0 g |
| PEG-200 dilaurate | 42.5 g |
| N-methylpyrrolidone | ad 100 ml |

The plasma samples taken after specific intervals of time are analysed. Whereas the formulations according to the invention achieve plasma concentrations in the range of from 40 to 100 ppb after 24 hours, the concentration of the active ingredient in the case of the formulation not according to the invention is below that range by at least a factor of two.

What is claimed is:

1. A composition for controlling parasites that attack productive livestock and domestic animals, which composition is parenterally injectable and contains from 0.1 to 10% of a compound of formula I

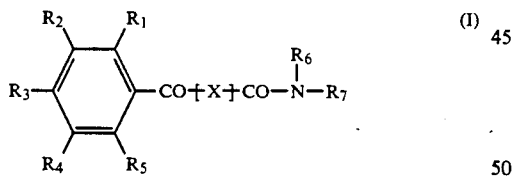

(I)

wherein
each of $R_1$, $R_2$, $R_3$ and $R_5$, independently of the others, is hydrogen, halogen, $C_1$-$C_6$alkyl, $C_1$-$C_6$haloalkyl, $C_1$-$C_6$alkoxy, $C_1$-$C_6$haloalkoxy or $C_1$-$C_6$alkylthio;

$R_4$ is hydrogen, halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio or NHR'; wherein R' is hydrogen, $R_8$CO— or $R_9$NHCO—, wherein $R_8$ is a $C_1$-$C_4$alkyl that is unsubstituted or mono- to tri-substituted by the same or different substituents from the group halogen, $C_1$-$C_4$alkoxy, $C_1$-$C_4$acyloxy and —COOG, wherein G is hydrogen, an alkali metal cation or an alkaline-earth metal cation, and $R_9$ is a $C_1$-$C_4$alkyl or phenyl group that is unsubstituted or mono- to tri-substituted by halogen;

X is —NH— or

wherein $Y^\oplus$ is an inorganic or organic cation;
$R_6$ is hydrogen or $C_1$-$C_6$alkyl; and
$R_7$ is an unsubstituted or substituted phenyl, the substituents being selected from the series halogen, alkyl, haloalkyl, alkoxy, haloalkoxy, alkylthio, haloalkylthio, alkenyl, haloalkenyl, alkynyl, haloalkynyl, alkylsulfinyl, alkylsulfonyl, haloalkylsulfinyl, haloalkylsulfonyl, alkylamino, dialkylamino and benzyl and also phenoxy which is substituted by substituents from the group consisting of halogen, haloalkyl, haloalkoxy and nitro, it being possible, in the case where $R_7$ is substituted phenyl, for cyano, N'-n-propyl-N'-phenylureido, an —O—CF$_2$—CF$_2$—O— bridge connecting two adjacent carbon atoms of the phenyl ring to one another, or phenoxy that is substituted by an —O—CF$_2$—CF$_2$—O— bridge connecting two adjacent carbon atoms of the phenyl ring to one another, also to be present as substituent;

from 0.1 to 60% of a compound of formula III

(III)

wherein n is an integer from 2 to 7 and R is a $C_6$-$C_{15}$alkyl which may be interrupted by an oxygen atom, from 2 to 90% of a physiologically tolerable non-ionic surfactant having a molecular weight of less than 20,000 and, if appropriate, as stabilising component, from 0.05 to 15% of an acid or a buffer mixture and ad 100% of a physiologically tolerable hydrophilic solvent or a mixture of physiologically tolerable hydrophilic and lipophilic solvents.

2. A composition according to claim 1, wherein each of $R_1$, $R_2$, $R_3$ and $R_5$, independently of the others, is hydrogen, halogen, $C_1$-$C_6$alkyl, $C_1$-$C_6$haloalkyl, $C_1$-$C_6$alkoxy, $C_1$-$C_6$haloalkoxy or $C_1$-$C_6$alkylthio;

$R_4$ is hydrogen, halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio or NHR'; wherein R' is hydrogen, $R_8$CO— or $R_9$NHCO—, wherein $R_8$ is $C_1$-$C_4$alkyl that is unsubstituted or mono- to tri-substituted by the same or different substituents from the group halogen, $C_1$-$C_4$alkoxy, $C_1$-$C_4$acyloxy and —COOG, wherein G is hydrogen, an alkali metal cation or an alkaline-earth metal cation, and $R_9$ is a $C_1$-$C_4$alkyl or phenyl group that is unsubstituted or mono- to tri-substituted by halogen;

X is —NH— or

wherein $Y^\oplus$ is an inorganic or organic cation;
$R_6$ is hydrogen or $C_1$-$C_6$alkyl; and
$R_7$ is an unsubstituted or substituted phenyl, the substituents being selected from the series halogen, alkyl, haloalkyl, alkoxy, haloalkoxy, alkylthio, haloalkylthio, alkenyl, haloalkenyl, alkynyl, haloalkynyl, alkylsulfinyl, alkylsulfonyl, haloalkylsulfinyl, haloalkylsulfonyl, alkylamino, dialkylamino and benzyl and also phenoxy is substituted by halogen, haloalkyl, haloalkoxy or by nitro.

3. A composition according to claim 1, wherein
each of $R_1$ and $R_5$, independently of the other, is hydrogen, fluorine, chlorine, methoxy or methylthio;
$R_3$ is hydrogen or fluorine and $R_4$ is hydrogen or $NH_2$;
$R_2$ is hydrogen, fluorine or chlorine;
X is —NH— or

wherein $Y\oplus$ is $Na\oplus$, $K\oplus$ or tetraalkylammonium, such as $(n-C_4H_9)_4N\oplus$, $(CH_3)_4N\oplus$, $(C_2H_5)_4N\oplus$ or $n-C_{16}H_{33}-N\oplus(CH_3)_3$;
$R_6$ is hydrogen or $C_1-C_3$alkyl, and
$R_7$ is unsubstituted phenyl or phenyl substituted by one or two halogen atoms and, additionally, by $C_1-C_6$haloalkoxy or by 2-pyridyloxy, the 2-pyridyloxy radical for its part being substituted by $CF_3$ and halogen.

4. A composition according to claim 1 that contains 1-n-dodecylazacycloheptan-2-one.

5. A composition according to claim 1 that contains 1-n-dodecylazacyclopentan-2-one.

6. A composition according to claim 1 that contains dimethyl sulfoxide as hydrophilic solvent.

7. A composition according to claim 1 that contains N-methylpyrrolidone as hydrophilic solvent.

8. A composition according to claim 1 that contains a lipophilic solvent from the group consisting of esters of carboxylic acids and liquid waxes.

9. A composition according to claim 1 that contains as stabilising component an acid selected from the group consisting of citric acid, ascorbic acid, lactic acid, acetic acid, malic acid and tartaric acid.

10. A method of controlling parasites that attack productive livestock and domestic animals, which method comprises injecting parenterally into the host organism attacked by parasites a composition containing from 0.1 to 10% of a compound of formula I

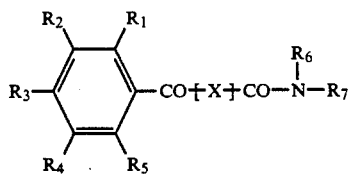

wherein each of $R_1$, $R_2$, $R_3$ and $R_5$, independently of the others, is hydrogen, halogen, $C_1-C_6$alkyl, $C_1-C_6$haloalkyl, $C_1-C_6$alkoxy, $C_1-C_6$haloalkoxy or $C_1-C_6$alkylthio;
$R_4$ is hydrogen, halogen, $C_1-C_6$alkyl, $C_1-C_6$haloalkyl, $C_1-C_6$alkoxy, $C_1-C_6$haloalkoxy, $C_1-C_6$alkylthio or NHR'; wherein R' is hydrogen, $R_8CO-$ or $R_9NHCO-$, wherein $R_8$ is a $C_1-C_4$alkyl that is unsubstituted or mono- to tri-substituted by the same or different substituents from the group halogen, $C_1-C_4$alkoxy, $C_1-C_4$acyloxy and —COOG, wherein G is hydrogen, an alkali metal cation or an alkaline-earth metal cation, and $R_9$ is a $C_1-C_4$alkyl or phenyl group that is unsubstituted or mono- to tri-substituted by halogen;
X is —NH— or

wherein $Y\oplus$ is an inorganic or organic cation;
$R_6$ is hydrogen or $C_1-C_6$alkyl; and
$R_7$ is an unsubstituted or substituted phenyl, the substituents being selected from the series halogen, alkyl, haloalkyl, alkoxy, haloalkoxy, alkylthio, haloalkylthio, alkenyl, haloalkenyl, alkynyl, haloalkynyl, alkylsulfinyl, alkylsulfonyl, haloalkylsulfinyl, haloalkylsulfonyl, alkylamino, dialkylamino and benzyl and also phenoxy which is substituted by substituents from the group consisting of halogen, haloalkyl, haloalkoxy and nitro, it being possible, in the case where $R_7$ is substituted phenyl, for cyano, N'-n-propyl-N'-phenylureido, an —O—CF$_2$—CF$_2$—O— bridge connecting two adjacent carbon atoms of the phenyl ring to one another, or phenoxy that is substituted by an —O—CF$_2$—CF$_2$—O— bridge connecting two adjacent carbon atoms of the phenyl ring to one another, also to be present as substituent;
from 0.1 to 60% of a compound of formula III

wherein n is an integer from 2 to 7 and R is a $C_6-C_{15}$alkyl which may be interrupted by an oxygen atom, from 2 to 90% of a physiologically tolerable non-ionic surfactant having a molecular weight of less than 20,000 and, if appropriate, as stabilising component, from 0.05 to 15% of an acid or a buffer mixture and ad 100% of a physiologically tolerable hydrophilic solvent or a mixture of physiologically tolerable hydrophilic and lipophilic solvents.

* * * * *